United States Patent [19]

Collins et al.

[11] Patent Number: 4,629,691
[45] Date of Patent: Dec. 16, 1986

[54] TRICYCLIC ANTIDEPRESSANT CONJUGATES WITH ANTIGENS AND ENZYMES

[75] Inventors: Christine G. Collins; Marcel R. Pirio, both of San Jose; Prithipal Singh, Sunnyvale, all of Calif.

[73] Assignee: Syntex (U.S.A.) Inc., Palo Alto, Calif.

[21] Appl. No.: 522,887

[22] Filed: Aug. 12, 1983

Related U.S. Application Data

[63] Continuation-in-part of Ser. No. 518,905, Sep. 1, 1983, abandoned.

[51] Int. Cl.[4] .......................... G01N 53/00; C12N 9/96
[52] U.S. Cl. ..................... 435/7; 260/112 R; 260/239 D; 424/85; 424/88; 435/4; 435/6; 435/18; 435/19; 435/21; 435/25; 435/26; 435/28; 435/188; 435/189; 435/192; 435/195; 514/2; 558/230; 558/250; 560/38; 562/443; 564/279; 564/367; 564/380; 436/543; 540/590; 530/362; 530/387
[58] Field of Search ....................... 260/239 D, 112 R; 435/188, 7, 4, 6, 18, 19, 21, 25, 26, 28, 183, 189, 192–195; 424/88, 85; 560/38; 562/443; 564/279, 367, 380; 558/230, 250; 514/2; 436/543

[56] References Cited

U.S. PATENT DOCUMENTS

| | | | |
|---|---|---|---|
| 3,846,409 | 11/1974 | Marx | 260/239 D |
| 3,998,810 | 12/1976 | Wiedemann et al. | 260/239 D |
| 4,207,307 | 6/1980 | Kaul et al. | 424/1 |
| 4,258,211 | 3/1981 | Engelhardt et al. | 564/380 |
| 4,275,160 | 6/1981 | Singh et al. | 435/188 |
| 4,495,281 | 1/1985 | Buckler et al. | 435/188 |

OTHER PUBLICATIONS

Ninth New Collegiate Dictionary (Meriam Webster), p. 224.

Aherne et al–Brit. J. Clin. Pharmacol. vol. 3 (1976), pp. 561–565.

*Primary Examiner*—Sam Rosen
*Attorney, Agent, or Firm*—Theodore J. Leitereg; Carole F. Barrett

[57] ABSTRACT

Tricyclic antidepressant functionalized compounds are provided for conjugation through a side chain to antigenic compounds, particularly poly(amino acids), and enzymes. The antigenic conjugates are employed for the production of antibodies and together with the enzyme conjugates find particular use in immunoassays for the determination or detection of the total amount of tricyclic antidepressants present in a sample.

20 Claims, No Drawings

TRICYCLIC ANTIDEPRESSANT CONJUGATES WITH ANTIGENS AND ENZYMES

This application is a continuation-in-part of our application Ser. No. 518,905, filed Sept. 1, 1983 and now abandoned.

BACKGROUND OF THE INVENTION

1. Field of the Invention

A number of tricyclic compounds find use in the treatment of depression. These tricyclic antidepressants include imipramine, desmethylimipramine (desipramine), amitriptyline, nortriptyline, protriptylene, and doxepin. In administering a tricyclic antidepressant, it is frequently necessary to ensure that the blood level of the antidepressant remains within a certain narrow concentration range in order to ensure effective dosage, while avoiding levels which may be toxic or produce undesirable effects. Furthermore, it is often necessary to detect potentially toxic levels of tricyclic antidepressants and their metabolites.

It is therefore desirable to provide a simple and rapid procedure for determining or detecting the levels of tricylic antidepressants in serum or other physiological fluids. The procedure should provide reproducible values and be specific for the tricyclic compounds which are measured. Thus, the procedure must be capable of distinguishing the tricyclic antidepressants from other drugs, which would otherwise give an erroneous result in an assay for the detection of tricyclic antidepressants.

2. Brief Description of the Prior Art

The tricyclic antidepressants are closely related chemically to one another. Techniques reported for the determination of amitriptyline in biological fluids include the use of thin layer chromatography, gas-liquid chromatography and GLC-mass spectrometry. Gifford, et al., *J. of Chrom.*, 105, 107-113 (1975); Gupta, et al., *Clin. Biochem.*, 9, 247-251 (1976); Nyberg and Martensson, *J. Chromatography*, 143, 491 (1977); Watson and Stewart, *J. Chrom.*, 134, 182 (1977); ibid. 132 155-159 (1977). Radioimmunnoassay has been reported for amitriptyline by Aherne, et al., *Br. J. Clin. Pharmac.*, 3, 561 (1976), Turner, *Lancet*, 180, 1316 (1977); and Aherne, et al., Lancet 1214 (1977). In Aherne, et al., ibid., a synthesis for an antigen for use as an immunogen for antibody formation is described, where nortriptyline is substituted with aminobutylene followed by conjugation to bovine serum albumin employing carbodiimide. In another antigen conjugate synthesis by Kaul, et al., *J. Anal. Tox.*, 1, 236 (1977), nortiptyline was conjugated to bovine serum albumin through a succinyl group. The resulting antibodies were found to have significant cross-reactivity with a number of other tricyclic drugs.

U.S. Pat. No. 4,275,160 describes imipramine derivatives and poly(amino acid) conjugates. U.S. Pat. Nos. 4,223,013 and 4,307,245 disclose amitriptyline conjugates to antigenic proteins and enzymes.

N-(2-carboxyethyl) derivatives of nortriptyline and desipramine are disclosed by Hubbard et al., *J. Pharm. Sc.*, 67, pp. 1571-1578 (1978) and by Hubbard et al., *Canadian Journal of Pharmaceutical Sciences*, 15, pp 89-93 (1980).

SUMMARY OF THE INVENTION

A synthetic procedure is provided for preparing tricyclic antidepressant derivatives wherein the methylaminopropyl side chain of a tricyclic antidepressant compound is functionalized for conjugation to proteinaceous materials, particularly antigenic and enzymatic poly(amino acids). The antigenic conjugate is employed as an immunogen for the production of antibodies for use in immunoassays. The enzyme conjugate is employed as a reagent in immunoassays for the determination of tricyclic antidepressant levels. The antibodies and enzyme conjugates are provided in combination in kits to be used for the rapid and accurate detection or determination of tricyclic antidepressants in serum as well as other physiological fluids.

DESCRIPTION OF THE PREFERRED EMBODIMENTS

Novel compounds are provided which are derivatives of a tricyclic antidepressant compound having a methylaminopropyl side chain. A non-oxo-carbonyl (substituted carbonyl) functionality (including nitrogen and sulfur analogs thereof) for linking to poly(amino acids), which are antigenic or enzymes is introduced into the side chain. The antigenic conjugates generally have a chain of at least 3 carbon atoms linking the methylaminopropyl side chain and the non-oxo-carbonyl and are employed as immunogens for the production of antibodies which are specific for tricylic antidepressant compounds, the antibodies finding use in immunoassays. We have found that the length of the chain, particularly with regard to the enzyme conjugates, is important in achieving crossreactivity with the tricyclic antidepressants and their metabolites, which crossreactivity is necessary to obtain the requisite sensitivity and reproducibility in an assay for the total concentration of tricyclic antidepressants in a sample. The enzyme conjugates of the present invention generally have a chain of at least four atoms linking the methylaminopropyl side chain and the non-oxo-carbonyl.

The enzyme conjugates are employed as reagents in enzyme immunoassays for the determination of the level of the total tricyclic antidepressant present in the sample.

Tricyclic antidepressant compounds which may be detected in an assay in accordance with the present invention are derivatives of dibenzazepine, dibenzocycloheptadiene, and dibenzoxepin and generally have the following formula

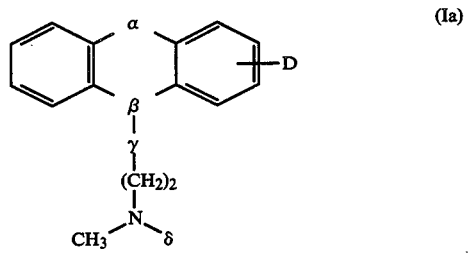

(Ia)

wherein:
α is $CH_2$-$CH_2$, $CH_2$-CH(OH), CH=CH, or $CH_2$-O;
β-γ is N-$CH_2$, C=CH, or N-CH(R) wherein R is alkyl of 1 to 3 carbon atoms, particularly $CH_3$;
δ is H or $CH_3$; and
D is hydrogen, hydroxy, or a halogen atom of atomic number 9 to 53, preferably 7 to 35, more preferably a chlorine atom.

Exemplary of such tricyclic antidepressant compounds are imipramine, desmethylimipramine, amitriptyline, nortriptyline, protriptylene, trimipramine, chlomipramine, and doxepin.

The following subgenus of tricyclic antidepressant compounds are susceptible to detection in the method of this invention:

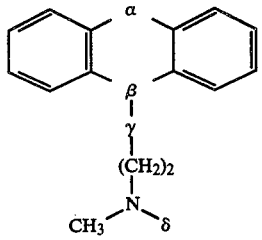
(Ib)

where:
α is $CH_2\text{-}CH_2$, $CH=CH$, or $CH_2\text{-}O$;
β-γ is $N\text{-}CH_2$ or $C=CH$; and
δ is H or $CH_3$.

For the most part, compounds of this invention will have the following formula

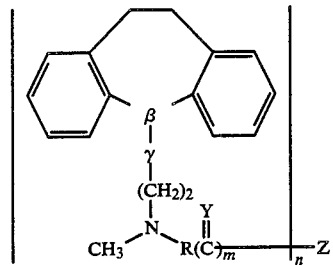
(II)

wherein:
β-γ is $N\text{-}CH_2$ or $C=CH$, preferably $N\text{-}CH_2$;
Y is chalcogen (oxygen or sulfur) or an imino group (NH);
R is a linking group of from 3 to 10 atoms other than hydrogen, usually 3 to 7 atoms other than hydrogen, containing an alkylene or alkenylene chain of at least 3 carbon atoms linked to the nitrogen atom of the annular side chain, which atoms are carbon, nitrogen, and chalcogen (oxygen and sulfur); when Z is an enzyme, generally from 4 to 10 atoms other than hydrogen including a chain of at least 4 atoms; usually from 7 to 8 atoms other than hydrogen, and, when Z is an antigenic poly(amino acid), generally from 3 to 6 atoms other than hydrogen, usually 3 to 5 atoms other than hydrogen; wherein a nitrogen atom, if present, is usually amido, and an oxygen atom, if present, is usually non-oxo-carbonyl (including sulfur analogs);
m is 0 or 1, preferably 1, being 1 when Z is other than poly(amino acid);
Z is a hydrogen atom, oxy including hydroxy, alkoxy of from 1 to 6 carbon atoms, or an activated ester group capable of amide formation with amino groups of a poly(amino acid) in an aqueous medium, e.g., N-oxy succinimide and p-nitrophenoxy, or a poly(amino acid), which is antigenic or an enzyme, which poly(amino acid) is joined by a bond to a methylene group when m is 0 and by an amide bond when m is 1. The poly(amino acids) will generally range from about 5,000 molecular weight, having no upper molecular weight limit, normally being less than 10,000,000 usually not more than about 600,000 daltons. There will usually be different ranges, depending on whether an antigen or an enzyme is involved, with antigens ranging from about 5,000 to $10^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one tricyclic antidepressant conjugate group per 500,000 molecular weight, more usually at least one conjugate group per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugate groups will generally be in the range of from about 2 to 10, usually in the range of 2 to 5; and
n is 1 when Z is other than a poly(amino acid) and is otherwise a number on the average between 1 and the molecular weight of Z divided by 500, more usually divided by 1,000 and frequently divided by 1,500, generally ranging from 1 to 500, preferably from 10 to 100, when Z is an antigen, and from 1 to 30, more usually 2 to 20, and preferably 2 to 16 when Z is an enzyme.

For those compounds where n is 1, the compounds will generally be of the formula:

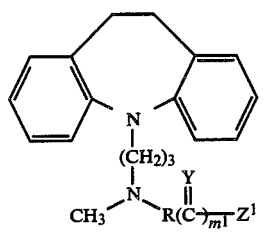
(III)

wherein:
R and Y have been defined previously;
$m^1$ is 1; and
$Z^1$ is a hydrogen atom, hydroxyl, alkoxyl of from 1 to 6, more usually 1 to 3, carbon atoms, particularly methyl and ethyl, or an oxy group forming an activated ester capable of reacting with an amine group of a poly(amino acid) under mild conditions in aqueous medium to form an amide, such as N-oxy succinimide or p-nitrophenoxy.

When Z is a poly(amino acid) other than an enzyme, the compounds will for the most part have the following formula:

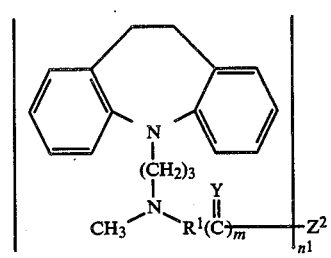
(IV)

wherein:

Y and m have been defined previously;

R$^1$ is an aliphatic linking group of from 3 to 6 carbon atoms, preferably 3 to 5 carbon atoms, preferably alkylene, such as ethylene, propylene, butylene, pentylene, hexylene, 2-methylpropylene, etc., alkenylenes such as 2-butenylene, 2-pentenylene, etc.;

n$^1$ is a number on the average between 1 and the molecular weight of Z$^2$ divided by 500, more usually divided by 1,000, and frequently divided by 1,500, generally ranging from 1 to 500, preferably from 10 to 100 when Z$^2$ is an antigen; and Z$^2$ is an antigenic poly(amino acid).

Various protein types may be employed as the poly(amino acid) antigenic material These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

Where Z is an enzyme the compounds will for the most part have the following formula

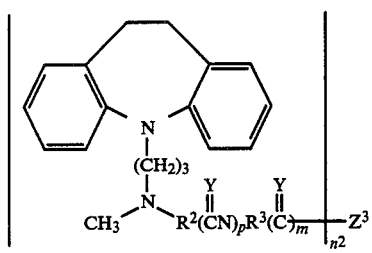

(V)

wherein:

Y and m have been defined previously;

p is 0 or 1;

R$^2$ is a saturated or unsaturated aliphatic linking group of from 3 to 4 carbon atoms, preferably alkylene, such as propylene, butylene, 2-methylpropylene, etc., and alkenylenes such as 2-butenylene, etc.;

R$^3$ is a saturated aliphatic linking group of from 1 to 3 carbon atoms, preferably alkylene, such as methylene, ethylene, and propylene; being 3 carbon atoms when p is 0; and n$^2$ is a number on the average between 1 and the molecular weight of Z$^3$ divided by 500, more usually divided by 1,000 and frequently divided by 1,500, generally ranging from 1 to 50, preferably 1 to 30, more usually 2 to 20, and preferably 2 to 16 when Z is an enzyme.

Z$^3$ is an enzyme.

The enzymes can be varied widely, depending upon the rapidity with which one desires a result and the physiological fluid in which the total tricyclic antidepressant level is to be measured. Primarily, the enzymes of choice, based on the I.U.B. classification are: Class 1. Oxidoreductases and Class 3. Hydrolases. Particularly in Class 1, the enzymes of interest are dehydrogenases of Class 1.1, more particularly 1.1.1, 1.1.3, and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

The synthetic scheme for preparing the subject compounds is set forth in the following flow chart:

REACTION SEQUENCE A

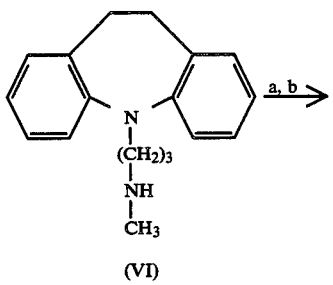

(VI)

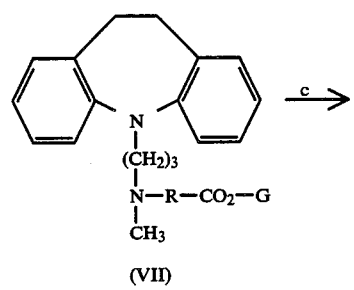

(VII)

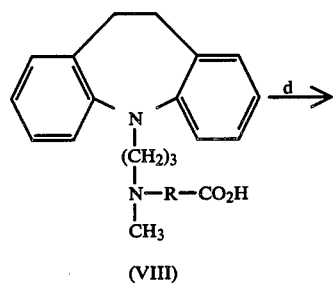

(VIII)

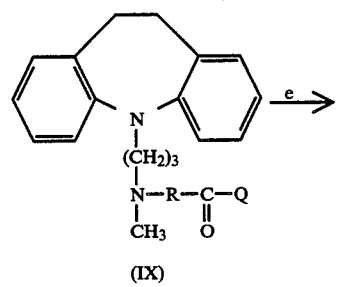

(IX)

-continued
REACTION SEQUENCE A

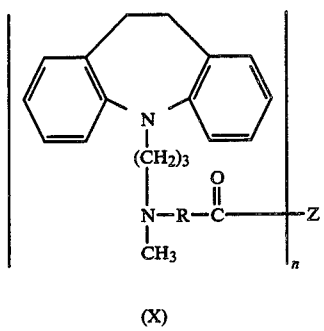

(X)

wherein:
(a) XRCO$_2$G where X is a halogen atom of atomic number 17 to 35, usually a bromine atom, and G is an alkyl group of from 1 to 3 carbon atoms;
(b) mild alkali such as carbonate;
(c) aqueous alkali such as sodium hydroxide;
(d) a reagent system for activating a carboxyl group with Q for reaction with amino groups of a poly(amino acid), wherein Q may be, for example, p-nitrophenoxy or N-hydroxy succinimide in a suitable anhydrous polar solvent such as dimethyl formamide;
(e) a poly(amino acid), e.g., Z, wherein n and Z have been previously defined.

In carrying out the above preparation desmethylimipramine (VI) is treated under mild alkaline conditions with XRCOG to give VII, which can be hydrolyzed under alkaline conditions to give acid VIII. The carboxyl group of VIII is activated by formation of an N-hydroxy succinimide or p-nitrophenoxy ester for reaction under aqueous conditions with amino goups of a poly(amino acid) to form amide linkages. Treatment of IX with the appropriate poly(amino acid) gives X.

For compounds of the formula V, the following synthetic scheme may be employed:

REACTION SEQUENCE B

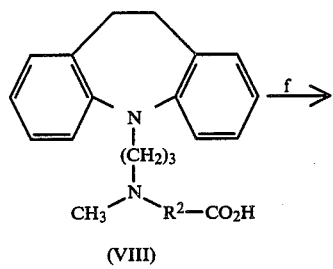

(VIII)

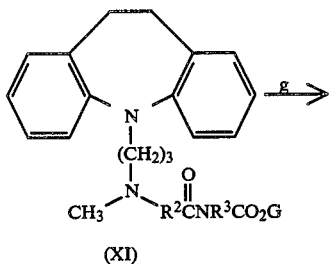

(XI)

-continued
REACTION SEQUENCE B

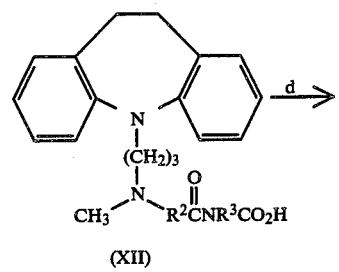

(XII)

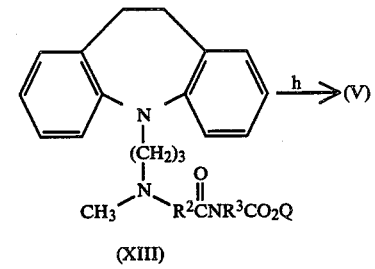

(XIII)

wherein:
R$^2$ has been defined previously;
(f) f an acid salt of H$_2$NR$^3$CO$_2$G, such as the hydrochloric acid salt, and an amine base such as triethylamine in an appropriate solvent, such as dichloromethane, wherein G and R3 have been defined previously;
(g) alkali such as sodium hydroxide;
(d) defined previously;
(h) an enzyme, i.e., Z$^3$.

In carrying out the above preparation, VIII is treated with an appropriate amino acid ester salt to give XI, which under alkaline hydrolysis is converted to XII. The carboxyl group of XII can be activated to XIII as described above for VIII (Reaction Sequence A). Reaction of XIII with an enzyme yields V.

By employing the above procedure desmethylimipramine is functionalized on the methylaminopropyl side chain to a compound which can be conjugated to antigenic or enzymatic poly(amino acids). The structure of desmethylimipramine is retained during the synthetic procedure and those elements of the structure which allow for formation of antibodies. The antibodies are capable of binding with II when Z is an antigenic poly(amino acid) or an enzyme and are specific for tricyclic antidepressants and capable of distinguishing tricyclic antidepressants, which are generally encountered in significant amounts in assays for total amounts of tricyclic antidepressant drugs, from otherdrugs. The antigenic compounds may be employed as immunogens for injection into a wide variety of vertebrates in accordance with conventional methods for the production of antibodies. Usually the animals are bled periodically with successive bleeds having improved titer and specificity, then reaching a maximum and diminishing in their specificity and titer.

As previously indicated, the antibodies and enzyme reagents prepared in accordance with the subject invention find particular use in immunoassays for the detection of, or the determination of levels of the total amount of tricyclic antidepressants in a sample. A description of a method for carrying out an immunoassay, which is a homogeneous enzyme immunoassay, may be found in U.S. Pat No. 3,817,837. The method involves combining the enzyme conjugate, the unknown sample suspected of containing tricyclic antidepressants and an antibody prepared as described above in an aqueous buffered medium at temperatures in the range of about 10° to 50° C., more usually from about 20° to 40° C., and determining the enzyme activity as compared to the enzyme activity of an assay medium having a known amount of tricyclic antidepressants.

EXAMPLES

The following examples are offered by way of illustration and not by way of limitation.

(All temperatures not otherwise indicated are in centigrade. All parts and percents are by weight except for mixture of liquids which are by volume.)

MeOH—methyl alcohol
UV—ultraviolet
TLC—thin layer chromatography
THF—tetrahydrofuran
DMF—dimethyl formamide
G-6-PDH—glucose -6- phosphate dehydrogenase
NADH—nicotinamide-adenine nucleotide
RSA—rabbit serum albumin
BSA—borine serum albumin
BgG—borine gamma globulin

EXAMPLE 1

Alkylation of Desmethylimipramine with Ethyl-4-bromobutyrate

Desmethylimipramine (DSI) free base, 6.7 g (0.0251 mole), obtained by dissolving 7.6 g DSI hydrochloride (USV Lbs. RHC No. 80315-A-4) in 600 ml of deionized water and treating the solution with 150 ml 1N NaOH. The white precipitate was extracted with several 600-ml portions of dichloromethane (until the extract did not turn blue when spotted on a silica gel plate presprayed with 5% $Ce_2(SO_4)_2.2H_2SO_4$ in 2N $H_2SO_4$, filtered and concentrated on a rotary evaporator, and then dried overnight under high vacuum <0.05 mm, 40° C.

DSI free base, 6.70 g (0.0251 mole), 9.8 (0.05031 mole) of ethyl-4-bromobutyrate, and 6.9 g (0.0503 mole) of potassium carbonate previously dried in an oven at 100° were added to 80 ml of distilled anhydrous dimethylformamide. The heterogeneous solution was maintained under moisture-free conditions and stirred at ambient temperatures for three days.

Reaction progress was monitored by dissolving an aliquot in water, extracting with $CH_2Cl_2$ and spotting on an Analtech silica gel GF plate, 1/9 - $MeOH/CH_2Cl_2$. Visualization by UV lamp and 5% $Ce(SO_4)_2.2H_2SO_4$ in 2N $H_2SO_4$ revealed three spots corresponding to starting material, product and by-product.

The reaction mixture was poured into a separatory funnel containing 250 ml $H_2O$ and extracted with 250 ml dimethyl ether and washed 10 times with 250 ml $H_2O$. The organic phase was dried over $MgSO_4$ and concentrated on a rotary evaporator and then on high vacuum overnight to give a light yellow oil.

Chromatography - Water 500 preparative LC-Prep pak - 500 (silica gel), eluant 4/6-hexane/ethyl acetate, flow rate 2.5 liter/min.

Volume of fractions varied from 250 ml to 1000 ml and progress was monitored by refractive index and TLC analysis Analtech silica gel GF 4/6 hexane-ethyl acetate.

Appropriate fractions were pooled and concentrated.

The column was washed with 1/9-methanol/ethyl acetate and more N-carboethoxy ester was eluted. Starting material was eluted with 1/9-methanol/dichloromethane.

EXAMPLE 2

Saponification of N-Carboethoxypropyldesmethylimipramine

N-Carboethoxypropyldesipramine, 5.0 g (0.1364 mole), from Example 1 was dissolved in 30/30/20 - MeOH/THF (distilled)/1N NaOH and stirred at room temperature overnight.

TLC analysis of reaction progress was conducted on an Analtech silica gel GF plate 1/9 - $MeOH/CH_2Cl_2$ and Merck silanized silica gel RP-2 1/9 $MeOH/CH_2Cl_2$.

The reaction product was concentrated on a rotary evaporator and the pH of the solution was brought, to 7.0 with conc. HCl. The material was extracted four times with 200 ml $CH_2Cl_2$. The organic phases were dried over $Na_2SO_4$, filtered, concentrated on a rotary evaporator and then under high vacuum, 4.59 g.

The above product (4.5 g) was dissolved in distilled $CH_2Cl_2$ and applied to the top of a column packed with $CH_2Cl_2$ and 200 g silica gel 60 silanized particle size 0.063–0.300 mm (70–230 mesh ASTM) (E. Merck Reagent), eluant 250 ml of $CH_2Cl_2$ (distilled), followed by a gradient of 1, 2, 3, 4, 5, 6, 7, 8, 9, 10% $MeOH/CH_2Cl_2$ (500 ml each). Fractions were pooled according to results of TLC 1/9 $MeOH/CH_2Cl$ on silica gel GF, visualized under a UV lamp and ceric sulfate-$H_2SO_4$ spray. The fractions were concentrated on a rotary evaporator and then on high vaccum to give a hygroscopic product (4.0 g).

Microanalysis: $C_{22}N_2O_2H_{28}.1 H_2O$: Calc. % C 71.62; % N 7.45; % H 7.60. Found % C 71.62; % N 7.45; % H 7.60.

EXAMPLE 3

Preparation of the Conjugate of N-Carboxypropyldesmethylimipramine and BSA

Distilled dicyclohexylcarbodiimide, 98 mg (0.475 mmol), N-hydroxysuccinimide (previously crystallized from ethylacetate), 1.46 mg (0.432 mmol) of N-carboxypropyldesmethylimipramine from Example 2 (previously dried over $P_2O_5$ at 100° C. and <0.05 mm overnight) and 6 ml of anhydrous dimethylformamide were combined, and stirred for 16 hours in a dessicator over $CaCl_2$ in a cold room ~0° C. A white precipitate formed within a few minutes.

The dimethylformamide solution was filtered through a Pasteur pipet containing a glass wool plug and was added dropwise to a stirring solution of 500 mg (0.0072 mmol) of Pentex Bovine Albumin (Miles Laboratories, Lot 39) and 45 ml of 0.1 M $Na_2CO_3$-$NaHCO_3$, pH 9.67, cooled to ~5° C. with an ice bath. The residual reaction vessel was rinsed with 2 ml dimethylformamide and added to the protein solution, then placed in the cold room for 22 hours.

The above conjugate solution was placed in a Spectrapor ® membrane tubing (distributed by Scientific Products) (cylinder diameter 20.4 mm, MW cutoff 6,000–8,000) and dialyzed 3 times against 4 liters of deionized water pH 9.8 with conc. NH4OH (≦4 drops/2 liters) for four hours.

The product was chromatographed on Sephadex G-50 (medium) with a bed volume 8 times the volume of antigen solution.

Appropriate fractions were pooled by UV monitoring and lyophilized to give BSA conjugate (520 mg) of hapten number 20.

EXAMPLE 4

Preparation of the Conjugate of N-Carboxypropyldesmethylimipramine and BgG

The procedure of Example 3 was repeated but with the following reagents: 500 mg (0.0031 mmol) BgG Pentex Bovine Gamma Globulin (Miles Laboratories, lot 1074 Fraction II), 63 mg (0.306 mmol) of dicyclohexylcarbodiimide, 35.2 mg (0.306 mmol) N-hydroxysuccinimide and 94 mg (0.279 mmol) of N-carboxypropyldesmethylimipramine (dried as in Example 3 for BSA conjugation) and 10 ml anhydrous dimethylformamide.

The above conjugate solution was placed in Spectrapor ® membrane tubing (cylinder diameter 20.4 mm, MW cutoff 6,000–8,000) and dialyzed 3 times against 4 liters deionized water pH 9.8.with conc. NH4OH.(≦4 drops/2 liters) for four hours.

The product was chromatographed on Sephadex G-50 (medium) with a bed volume 8 times the volume of antigen solution.

Appropriate fractions were pooled by UV monitoring and lyophilized to give BgG conjugate (475 mg) of hapten number 30.

EXAMPLE 5

Preparation of N-Carboglycylpropyldesmethylimipramine Ethyl Ester

N-carboxypropyldesmethylimipramine, 4.33 g (0.0123 mole), from Example 2 (previously dried over $P_2O_5$ at 100° C., <0.05 mm overnight), 3.43 g (0.0246 mmol) glycine ethyl ester.HCl and 1.8 ml distilled triethylamine were taken up in 75 ml of reagent grade dichloromethane. To this stirring solution was added 2.78 g (0.01353 mole) N,N′-dicyclohexylcarbodiimide. A precipitate formed within 10–15 minutes. The reaction was stirred at ambient temperature overnight.

TLC analysis of reaction progress on Analtech silica gel GF 1/9 - MeOH/CH2Cl2 was visualized using a UV lamp and 5% Ceric sulfate in 2N $H_2SO_4$.

The precipitate was removed by passing the reaction mixture through a fine glass funnel. Concentration of the filtrate on a rotary evaporator left an oil and precipitate. This was taken up in ethyl acetate and again filtered and concentrated. The residue was dissolved in CH2Cl2 and extracted several times with 300 ml water, dried over MgSO4 and concentrated on a rotary evaporator and then on high vacuum to give 5.8 g of product.

The product was chromatographed on HPLC Water 500 prep LC - silica gel Prep pak - 500, eluant 10% absolute ethanol - dichloromethane, and flow rate 2.5 liter/min. Fractions were monitored via refractive index.

After pooling of appropriate fractions monitored with Analtech silica gel GF - 1/9 MeOH CH2Cl2, 4.2 g of product was recovered.

EXAMPLE 6

Saponification of N-Carboglycylpropyldesmethylimipramine Ethyl Ester

N-carboglycylpropyldesmethylimipramine ethyl ester from Example 5 (3 gm, 0.00686 mole) was dissolved in 30 ml methanol, 30 ml distilled THF and 30 ml 1N NaOH. The solution was stirred at ambient temperature overnight.

TLC of the reaction product with Analtech silica gel GF and absolute methanol revealed saponification was complete.

Most of the organic solvent was removed on a rotary evaporator and the pH of the aqueous solution was adjusted to 7.0 with conc. HCl. The solution was frozen and lyophilized leaving a light yellow solid. The product was extracted from the salts by washing with methanol until filtrate was negative for product. The filtrate was monitored by spotting a TLC plate previously sprayed with ceric sulfate spray; the product gave a deep blue color. Weight product recovered was ~2.7 gm.

The product was chromatographed on a column wet packed with 65 g silica gel 60–200 mesh Baker reagent (J. T. Baker Chemical) and dichloromethane. The product was taken up in dichloromethane and applied to the top of a column, and a step gradient system was employed for elution as follows: 250 ml CH2Cl2; 250 ml each 10, 20, 30, 40, 50, 60, 70% MeOH-CH2Cl2; products started to elute in the 50% MeOH-CH2Cl2 fractions.

TLC of fractions was conducted on an Analtech silica gel GF plate with absolute methanol as an eluant visualized by UV lamp and 5% $Ce(SO_4)_2 \cdot 2H_2SO_4$ in 2N $H_2SO_4$ spray.

Appropriate fractions were pooled, concentrated on a rotary evaporator and then on high vacuum giving a white foam (2.3 g).

The compound (830 g) was applied to the top of a column containing Merck silica gel 60 silanized particle size 0.063–0.200 mm (70–230 mesh ASTM).

The column dimensions were 3×22 cm wet packed with distilled dichloromethane. Elution was conducted with a step gradient, initially 200 ml CH2Cl2 (a yellow impurity eluted), 100 ml each of 2, 4, 6, 8% MeOH-CH2Cl2., then 400 ml 10% MeOH-90%CH2Cl2. Solvents were distilled or chromatographic grade solvents were used in chromatography.

TLC analysis of fractions on Analtech silica gel GF plates with MeOH as eluant, visualized with 5% $Ce_2(SO_4)_2 \cdot 2H_2SO_4$ in 2N $H_2SO_4$. Appropriate fractions were pooled, concentrated, and dried under high vacuum leaving a white foam 760 mg.

A small sample was dried over $P_2O_5$ at 100° C. at <0.05 mm for 24 hours and microanalysis determined.

Microanalytical Data: $C_{24}N_3H_{31}O_3 \cdot 0.5\ H_2O$: Calc: % C 69.11; % H 7.48; % N 10.04. Found: % C 69.11; % H 7.48; % N 10.04.

EXAMPLE 7

Preparation of the Conjugate of N-Carboqlycylpropyldesmethylimipramine and G-6-PDH 25 mg (0.0610 mmol) of the acid from Example 6 was placed in a reaction vial and dried in an Abderhalden over $P_2O_5$ at 100° C., <0.1 mm for 24 h. To this vial was added a Teflon ® stirring bar, 7.71 (0.0671 mmol)

of NHS (previously crystallized from ethyl acetate), 13.8 mg (0.0671 mmol) of N, N$^1$-dicyclohexylcarbodiimide (previously distilled) and 250 μl of anhydrous DMF (distilled over CaO and stored over 3A molecular sieves). A serum cap was used to seal the vial, and within a few minutes a precipitate formed. The reaction vessel was placed in a CaCl$_2$ dessicator; the contents of the reaction vessel were stirred at room temperature overnight (16–20 h).

Into a reaction flask was introduced 7.0 ml G-6-PDH, 4.0 mg/ml in Tris (0.055 molar), 140 mg glucose-6-phosphate Na$_2$, 280 mg NADH and 2.1 ml DMF. The above activated hapten solution (90 μl) was added over a period of about 1.25 h. The reaction product was chromatographed on a Sephadex G-50 column and eluted with 0.055 M Tris buffer. The enzyme conjugate had 52% of the original activity of the enzyme conjugate and was 48% inhibitable with saturating amount of anti-desmethylimipramine sera.

EXAMPLE 8

In order to demonstrate the efficacy of compounds prepared in accordance with the subject invention, the antibodies and the enzyme conjugate were employed in a number of assays for total tricyclic antidepressant content. In carrying out the assay, a Gilford 300 N microsample spectrophotometer was employed with a Thermocuvette with a flow cell. All readings are made at 340 mn. The following solutions are prepared as reagents for use in the assay.

Buffer:
  0.055 M tris-HCl pH 8.1 (RT)
Enzyme conjugate:
  Buffer
  0.9% NaCl
  1.0% β-lactoglobulin, 32 mmols per liter of glucose-6-phosphate, pH 6.2 (RT)
  Sufficient enzyme conjugate from Example 7 to give a maximum rate of ΔOD equal to 600–900 in the assay medium
Assay buffer:
  Buffer
  0.5% NaCl
  0.01% (v/v Triton X-100, pH 8.1 (RT)
Antibody Reagent:
  Buffer
  0.1% β-lactoglobulin
  G6P(Na) 0.066 M
  NAD 0.04 M, pH 5 (RT)
  Antibodies produced in response to the compound of Example 3 optimized for assay
  (All % indicated are w/v g/ml.)

The protocol employed for carrying out an assay was as follows: A sample, 50 microliters, was drawn up into a diluter and dispensed with 250 microliters of the assay buffer into a one milliliter Croan cup. A 50 μl aliquot of the diluted sample was drawn up and dispensed wit a 250 μl portion of assay buffer into a second Croan cup. Into the second Croan cup was introduced 50 μl of the assay buffer, followed by the addition of 50 μl of the enzyme reagent and 250 μl of the assay buffer. Immediately after the enzyme addition, the entire sample was aspirated into the flow cell. After 15 seconds, a first reading was taken, followed by a second reading reading, after a 30 second interval. The results were reported as the difference in absorbance ×2.667.

| Sample Concentration of Total Tricyclic Antidepressants (mg/ml) | | | | |
|---|---|---|---|---|
| AMI | NOR | IMI | DMI | ΔOD |
| 400 | 0 | 0 | 0 | 634 |
| 300 | 100 | 0 | 0 | 634 |
| 200 | 200 | 0 | 0 | 632 |
| 100 | 300 | 0 | 0 | 634 |
| 0 | 400 | 0 | 0 | 633 |
| 0 | 0 | 400 | 0 | 636 |
| 0 | 0 | 300 | 100 | 637 |
| 0 | 0 | 200 | 200 | 639 |
| 0 | 0 | 100 | 300 | 635 |
| 0 | 0 | 0 | 400 | 637 |

AMI — amitriptyline;
NOR — nortriptyline;
IMI — imipramine;
DMI — desmethylimipramine An assay was performed substantially as described above employing a conjugate of N-carboxypropyldesmethylimipramine and G-6-PDH (prepared from N-carboxypropyldesmethylimipramine and G-6-PDH following the procedures similar to Example 7) in place of a conjugate of N-carboglycylpropyldesmethylimipramine and G-6-PDH. Meaningful assay results could not be obtained with the former conjugate.

The subject assay provides for a sensitive method for determining the total tricyclic antidepressant content in biological fluids such as serum. The subject invention provides reagents specific for the tricyclic antidepressants and potentially toxic metabolites thereof, which allows for a substantial range of changes in enzyme activity with change in concentration of the tricyclic antidepressants. The method is rapid, the results are reproducible, and the protocol is simple and relatively free of technician introduced error and can be performed substantially in the same manner as an enzyme assay.

Although the foregoing invention has been described in some detail by way of illustration and example for purposes of clarity and understanding, it will be obvious that certain changes and modifications may be practiced within the scope of the appended claims.

What is claimed is:

1. A compound of the formula:

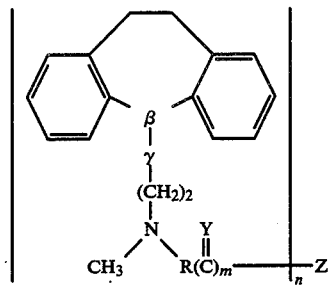

wherein:
  β-γ is N-CH$_2$ or C=CH;
  Y is an oxygen or sulfur atom or imino;
  R is a linking group of from 3 to 10 atoms other than hydrogen comprising carbon, nitrogen, oxygen and sulfur containing an alkylene or alkenylene chain of at least 3 carbon atoms linked to the nitrogen atom of the annular side chain; when Z is an enzyme, R is a linking group of 4 to 10 atoms other than hydrogen having a chain of at least 4 atoms;

m is 0 to 1, being 1 when Z is other than poly(amino acid);

Z is a hydrogen atom, oxy, an activated ester capable of amide formation with amino groups of a poly(amino acid) in an aqueous medium, or an antigenic poly(amino acid) or enzyme, with the proviso that, if $\beta$-$\gamma$ is C=CH, m is 1, Y is oxygen, and Z is an antigenic poly(amino) acid, then Z is bonded to the carbonyl group by an amide linkage; and n is 1 when Z is other than a poly(amino acid) and is otherwise a number on the average between 1 and the molecular weight of Z divided by 500.

2. The compound of claim 1 wherein $\beta$-$\gamma$ is N-CH$_2$.

3. The compound of claim 1 wherein Z is an antigenic poly(amino acid).

4. The compound of claim 1 wherein Z is bovine serum albumin.

5. The compound of claim 1 wherein Z is bovine gamma globulin.

6. The compound of claim 1 wherein Z is an enzyme.

7. The compound of claim 6 wherein Z is glucose-6-phosphate dehydrogenase.

8. Antibodies produced in response to the compound of the formula of claim 1 wherein Z is an antigenic poly(amino acid) which binds to said compound, to tricyclic antidepressants, or to the compound of claim 1 wherein Z is an enzyme.

9. The compound of claim 1 wherein the oxy is selected from hydroxy or alkoxy of from 1 to 6 carbon atoms.

10. A compound of the formula:

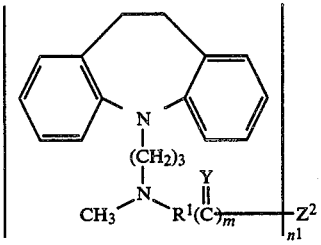

wherein:
Y is oxygen, sulfur or imino;
m is 0 or 1;
R' is an aliphatic linking group of from 3 to 6 carbon atoms;
Z$^2$ is a poly(amino acid) other than an enzyme
n$^1$ is a number on the average between 1 and the molecular weight of Z$^2$ divided by 500.

11. The compound of claim 10 wherein Z$^2$ is an antigenic poly(amino acid).

12. The compound of claim 10 wherein Z$^2$ is bovine serum albumin.

13. The compound of claim 10 wherein Z$^2$ is bovine gamma globulin.

14. Antibodies produced in response to the compound of claim 11 which are capable of binding with the compound of claim 11 and to tricyclic antidepressants.

15. A compound of the formula:

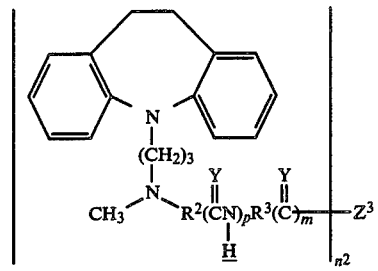

wherein:
Y is an oxygen or sulfur atom or imino;
P is 0 or 1;
R$^2$ is an aliphatic linking group of from 3 to 4 carbon atoms;
R$^3$ is an aliphatic linking group of from 1 to 3 carbon atoms; being 3 carbon atoms when p is 0;
m is 0 or 1;
Z$^3$ is an enzyme; and
n$^2$ is a number on the average between 1 and the molecular weight of Z$^3$ divided by 500.

16. The compound of claim 15 wherein Z is glucose-6-phosphate dehydrogenase.

17. The compound of claim 15 wherein Y is oxygen, p is 1, R$^2$ is propylene, R$^3$ is methylene, and m is 1.

18. A method for determining the total amount of tricyclic antidepressants present in a sample suspected of containing such tricyclic antidepressants, which comprises:

(a) combining the sample, an antibody produced in response to the compound of the formula of claim 1 wherein Z is an antigenic poly(amino acid) which binds to said compounds, or a compound of the formula of claim 1 wherein Z is an enzyme, (b) incubating the combination; and (c) determining the enzyme activity of the sample and comparing the enzyme activity with the enzyme activity of an assay medium having a known amount of tricyclic antidepressants.

19. The method of claim 18 wherein the tricyclic antidepressants have the following formula:

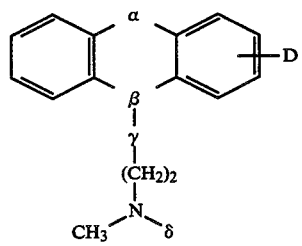

(Ia)

wherein:
$\alpha$ is CH$_2$-CH$_2$, CH$_2$-CH(OH), CH=CH, or CH$_2$-O;
$\beta$-$\gamma$ is N-CH$_2$, C=CH, or N-CH(R) wherein R is alkyl of 1 to 3 carbon atoms;
$\delta$ is H or CH$_3$; and
D is a hydrogen atom, hydroxy, or a halogen atom of atomic number 9 to 53.

20. The method of claim 18 wherein the tricyclic antidepressants have the following formula:

17
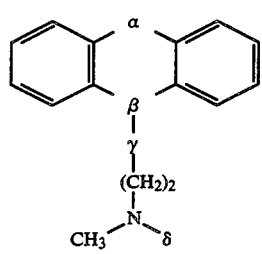
wherein:
α is $CH_2$-$CH_2$, CH=CH, or $CH_2$-O;
β-γ is N-$CH_2$ or C=CH; and
δ is H or $CH_3$.
* * * * *
18
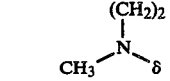
wherein:
α is $CH_2$-$CH_2$, CH=CH, or $CH_2$-O;
β-γ is N-$CH_2$ or C=CH; and
δ is H or $CH_3$.
* * * * *